(12) United States Patent
Cochrane (10) Patent No.: US 8,454,233 B2
(45) Date of Patent: Jun. 4, 2013

(54) DEVICE AND METHOD FOR THE NON-DESTRUCTIVE TESTING OF OBJECTS

(75) Inventor: David Robb Cochrane, Sint Job Int Goor (BE)

(73) Assignee: Georg Hafner, Zurich (CH)

( * ) Notice: Subject to any disclaimer, the term of this patent is extended or adjusted under 35 U.S.C. 154(b) by 374 days.

(21) Appl. No.: 12/663,324

(22) PCT Filed: Apr. 8, 2008

(86) PCT No.: PCT/CH2008/000157
§ 371 (c)(1),
(2), (4) Date: Apr. 27, 2010

(87) PCT Pub. No.: WO2008/148228
PCT Pub. Date: Dec. 11, 2008

(65) Prior Publication Data
US 2010/0272240 A1    Oct. 28, 2010

(30) Foreign Application Priority Data

Jun. 7, 2007   (WO) ............... PCT/CH2007/000286
Sep. 26, 2007  (WO) ............... PCT/CH2007/000476

(51) Int. Cl.
*H05G 1/26* (2006.01)
(52) U.S. Cl.
USPC .......................................... 378/197; 378/167
(58) Field of Classification Search
USPC .................. 378/167, 57, 51, 53, 55, 193, 196, 378/197
See application file for complete search history.

(56) References Cited

U.S. PATENT DOCUMENTS

| 2,965,761 | A | | 12/1960 | Horvath |
| 3,983,400 | A | * | 9/1976 | Donovan ................. 378/181 |
| 5,237,598 | A | | 8/1993 | Albert |
| 7,078,702 | B2 | | 7/2006 | Ringermacher et al. |
| 2004/0016886 | A1 | | 1/2004 | Ringermacher et al. |

FOREIGN PATENT DOCUMENTS

| GB | 1219837 | 1/1971 |
| GB | 2251047 | 6/1992 |
| JP | 62-49246 | 3/1987 |
| JP | 3-16562 | 1/1991 |
| JP | 4-3438 U | 1/1992 |
| JP | 6-222484 | 8/1994 |
| JP | 9-89810 | 4/1997 |
| JP | 09-304301 | 11/1997 |
| JP | 2001-74672 | 3/2001 |
| JP | 2004-125450 | 4/2004 |
| JP | 2004-177230 | 6/2004 |
| JP | 2004-333409 | 12/2009 |

OTHER PUBLICATIONS

Dave Cochrane, "New Radiography System Overcomes Problems Caused by Scaffolding", The Journal of the British Institute of Non-Destructive Testing, "Insight", vol. 48, No. 5, May 2006.

* cited by examiner

*Primary Examiner* — Hoon Song
(74) *Attorney, Agent, or Firm* — Rankin, Hill & Clark LLP (57) ABSTRACT

A device for non-destructive testing of objects, particularly pipes in oil refineries, having a first positioning device for positioning a collimator including a radioactive radiation source near an object to be tested, and a second positioning device for positioning a film carrier near the object to be tested. The first positioning device may be anchored or placed with a lower end on a substantially flat base surface, wherein the collimator is attached to the opposite, upper end of the first positioning device. Before the exposure, the radiation source may be guided towards the collimator via a delivery tube such that no radiation is able to be emitted from the device during the placement of the first positioning device.

4 Claims, 5 Drawing Sheets

DEVICE AND METHOD FOR THE NON-DESTRUCTIVE TESTING OF OBJECTS

BACKGROUND OF THE INVENTION

1. Field of the Invention

The invention relates to the field of non-destructive testing, in particular of conduits of industrial plants such as oil refineries, in the chemical industry, processing industry, etc. It relates to a device and a method for the non-destructive testing of objects according to the preamble of the respective independent patent claims.

2. Description of Related Art

With the testing of pipes in oil refineries, at present, frameworks are set up in order to make X-ray photographs of the pipes. Film plates and X-ray radiation sources, from the framework, are firmly connected to the pipe and the framework. As a rule, the operating personnel must leave the framework on triggering photographing. The method is time-consuming and necessitates the standstill of the plant, with correspondingly high resulting costs. This analogously applies to the testing of pipes and containers in other branches of industry.

JP 09-089810 shows an apparatus for the inspection of pipes. The apparatus comprises a motorically driven joint arm or manipulator, which on the one hand comprises a collimator for receiving a radiation source and on the other hand a tiltable holding plate for an X-ray film. For photographing, the joint arm is traversed below a pipe, the X-ray plate set upright behind the pipe and the radiation source transported into the collimator. The device is mechanically complicated and may only be applied in a limited manner.

Devices for transporting a radiation source from a container into a collimator and back are known for example in GB 2 251 047 and U.S. Pat. No. 2,965,761.

BRIEF SUMMARY OF THE INVENTION

It is therefore the object of the invention to provide a device and a method for the destruction-free testing of objects of the initially mentioned type, which alleviates the disadvantages mentioned above.

These objects are achieved by a device and a method for the non-destructive testing of objects with the features of the respective independent patent claims.

The device for the non-destructive testing of objects comprises a first positioning means for positioning a collimator for receiving a voltage source at an object to be tested (i.e. against the object or in the direct vicinity of the object), as well as a second positioning means for positioning a recording carrier at the object to be tested. The first positioning means may be anchored or set up with a lower end on a rest surface, wherein the collimator is attached on the opposite upper end of the first positioning means.

With this, it is possible to create photographs of the pipes to be tested, without frameworks having to be assembled and dismantled. Moreover, one may make photographs in small spaces, in shafts or at inaccessible locations.

Preferably, the radiation source is a radioactive radiation source, preferably a body which contains radioactive material. Thus one may make X-ray photographs of objects to be tested with a recording medium in the recording carrier, said recording medium being sensitive to radioactive radiation.

In a preferred embodiment of the invention, the radiation source may be led via a delivery tube to the collimator and be removed from this, preferably by way of a cable pull. Thereby, the radiation source, when it is not located in the collimator, is stored in a shielded isotope container or storage container, wherein the storage container is arranged distanced from the collimator. The outer casing of the radiation source has the shape of a roughly cylindrical pill or capsule. The delivery tube is preferably fixed on the first positioning means, but may however also be guided and held by way of a separate rod. A pneumatic conveying of the radiation source by way of blowing in air through the delivery tube is also possible, but is not preferred for reasons of safety.

The invention is not limited to the use of a cable pull. In a further embodiment of the invention, it may also comprise other means for transporting a radiation source to a given location, or means for activating a radiation source which, for example, is located at a defined location in a shielded manner.

Preferably, parts of the device, in particular all external or touchable parts, are manufactured of materials which do not produce sparks, in particular of brass, aluminium and/or plastic. This above all concerns supporting tubes and rods of the two positioning devices, but also includes nuts, screws or bolts for connecting and locking the rods, as well as further small parts. Such small parts may be manufactured of steel and for this, be completely or partly coated with another material not producing sparks, such a plastic or rubber. If the frame is assembled on wheels, then preferably antistatic, i.e. conductive wheel materials are used. With this, work is possible in surroundings in which there is a danger of explosion.

Preferably, the length of the first positioning means and of the second positioning means is more than one and a half or two meters, for example up to six or to nine meters. This length is the distance between the base, on which the first positioning means rests, and the collimator, and analogously, the distance between a foot of the second positioning means and the recording carrier. With this, the length of the delivery tube is also at least 2 to 5 meters or more, i.e. accordingly longer by one to, for example, five meters longer, since the delivery tube must be distanced to the foot of the first positioning means for practical reasons.

The second positioning means preferably comprises a holding tube for positioning the recording carrier with respect to the object to be tested, wherein the second positioning means may be fastened at various locations of the recording carrier by way of a releasable connection. The releasable connection is for example a Velcro connection between a connection plate of the holding tube and the recording carrier. With this, it is also possible to rest or press the recording carriers against the object to be tested, without the recording carrier being tilted away. For this, the connection location between the holding tube and the recording carrier on the surface of the recording carrier is selected such that the recording carrier bears in a stable manner against the object to be tested, in the desired position.

Instead of the Velcro connection, basically one may also select another type of the connection, which permits an essentially free positioning of the connection plate on the recording carrier: for example by way of magnets;

by way of a plate fastened on the recording carrier, with a hole pattern onto which plate the connection plate may be screwed at different locations, by way of a series of rubber cables, which span over the rear side of the recording carrier and below which the connection plate may be pushed at various locations.

The Velcro connection however has the advantage that it is lightweight, the recording carrier may be covered with this all around and on all sides and by way of this also acts as a cushion, and that guide bodies may also be fastened with it.

The first positioning means is preferably movable separately from the second positioning means and may be positioned independently.

Preferably, moreover the recording carrier may be rotated with respect to the holding tube of the second positioning means about an axis perpendicular to the axis of the holding tube. By way of this, the recording carrier, on leaning against the object to be tested, may rotate into a yet more stable position. This position is, for example, parallel to a surface or a tube or a plane of the tube, depending on the geometry of the object to be tested.

In a further preferred embodiment of the invention, the recording carrier comprises guide bodies for supporting and guiding the recording carrier on the object to be tested. Thereby, the guide bodies may be adjustably fastened on the side of the recording carrier, said side being distant to the holding tube (thus on the side which is to face the object to be tested). The guide bodies are preferably adjustably fastenable on the recording carrier, preferably by way of Velcro connections. With this, the position of the recording carrier with respect to the object to be tested may be defined by way of the guide bodies being placed on the recording carrier according to the desired position on the object to be tested, before the positioning of the recording carrier.

In the method for the use of the mentioned device, the following steps are carried out:

setting up the first positioning means with the collimator on one side of the object to be tested;

setting up the second positioning means with the recording carrier at a side of the object to be tested, which lies opposite the collimator triggering a recording by way of activating the radiation source.

Thereby preferably the step of the triggering of a recording comprises the following steps:

transporting the radioactive radiation source by way of a delivery tube to the collimator;

transporting the radiation source back out of the collimator to a shielded container by way of the delivery tube.

The step of setting up the first positioning means preferably comprises the following steps:

setting and fixing a planned distance between the collimator and the object to be tested, by way of adjusting the mechanical guide, optionally also by way of the selection of the positioning of the collimator on the first positioning means;

optionally extending a telescope rod until the collimator is at the desired height; and moving the first positioning means, preferably by hand, until the mechanical guide bears on the object to be tested, in the desired position.

A preferred variant: of the method thereby comprises the following steps:

setting and fixing a planned angle between a rod and an extension arm (or simply arm) with a mechanical guide;

extending or lifting a rod, preferably by hand, into the vicinity of the object to be tested; and tilting the rod, preferably by hand, about a rotation point or a rotation axis, against the object to be tested, until the mechanical guide bears against the object to be tested.

The setting and fixing of distances and angles mentioned above is preferably effected in a manual manner. The movement or tilting of the first positioning means is likewise effected preferably by way of one or more persons who hold and move a lower end of the first positioning means, and by way of this move the guide and collimator, which are arranged at the upper end, into the desired measurement position.

The step of setting up the second positioning means preferably has the following steps:

positioning the connection plate of the second positioning means on the recording carrier in a position which may be selected freely on a first surface of the recording carrier, and fixing the connection plate by way of a releasable connection;

optionally: positioning guide bodies on a second surface of the recording carrier;

moving and resting the recording carrier against the object to be tested; optionally by way of a guide which is effected by way of the guide bodies bearing on the object to be tested.

Thereby, the position of the connection plate on the recording carrier is selected such that this does not tilt away, on the object to be tested. The recording carrier preferably rotates freely about an axis with respect to a rod of the second positioning means, so that the recording carrier bears on the object to be tested in a stable position.

The movement and resting of the second positioning means is likewise effected preferably by way of one or more persons who hold and move a first, typically lower end of the second positioning means, and by way of this move the recording carrier arranged at the second, typically upper end, into the desired measurement position.

In a further preferred embodiment, the recording carrier is flexible and pliable and by way of this may be pressed against the inner wall or the outer wall of a container. With this pressing or pressure application, the recording carrier deforms, and adapts to the concave or convex shape of the container and bears on the wall. On pressing onto an inner side, the already described second positioning means may be applied.

On fastening on the outer side of a container, in a preferred embodiment of the invention, magnets for fixing the recording carrier are used. The magnets may be separate parts and may be applied from the outside against the recording carrier or the magnets may be installed in the recording carrier in a fixed manner. In another embodiment of the invention, the recording carrier is pressed with at least two separate rods as an edge mounting, against the outer side.

A corresponding method for positioning a recording carrier thus comprises the steps:

positioning and fixing the recording carrier on the outer wall of the container by way of magnets or positioning and fixing the recording carrier on the outer wall of a container by way of the edge mounting.

The recording carrier according to a further embodiment of the invention may be fastened on an elastically spreadable fork as an edge mounting. The fork reaches up to the outer edges of the recording carrier and is rotatably fastened on the left and right edge of the recording carrier. The recording carrier, thus, is bendable and arranged between the ends of the fork. On pressing on a convex body, the fork closes a little and the recording carrier sags against the fork and thus bears on the convex body.

The first positioning means in a preferred embodiment of the invention comprises a mechanical guide for centring the collimator with respect to an object to the tested, by way of the mechanical guide being pressed against the object to be tested. This guide may be a fork widening in a Y-shaped manner, or may be adapted in another manner to the shape of the object to be tested. Furthermore, the mechanical guide effects a distancing of the collimator to the object to be tested, thus permits an exact setting of the distance between the collimator and the object to be tested. With this, the distance may be set by way of displacing the mechanical guide with respect to an object, on which the collimator is fastened.

This exact distancing is advantageous, depending on the applied measurement principle. For example, with a lateral X-ray photograph of a pipe, the geometry of the image or projection onto the X-ray film is known on account of the sellable distance between the collimator to the pipe on the one hand, and the fact that a recording carrier is pressed against the pipe. For example, a wall thickness in the X-ray picture may be measured, and the actual wall thickness of the pipe may be computed thanks to the known geometry.

Preferably, the collimator as well as the mechanical guide are fastened on a rod, and the collimator is selectively fastenable above or below the mechanical guide. With this, the relative position between the collimator and the guide may be adapted to the geometry of the object to be tested.

In a further preferred embodiment of the invention, the first positioning means comprises a rod which may be set up in a tiltable manner and for this may be tilted about a rotation axis or a rotation point. Preferably for this, the rod is fastened on a joint foot in a rotatable manner about an axis, or is fastened on a bipod stand. Moreover, the first positioning means further comprises an adjustable joint between the rod and an extension arm, by which means a mechanical guide fastened on the extension arm is movable in a selectable angle against an object to be tested and may be leaned on the object to be tested. By way of this, it is possible to apply the rod also in restricted conditions in an installation. An oblique position of the rod which arises because of the tilting, is compensated for by way of the joint between the rod and the extension arm, so that the extension arm may be positioned with the collimator in a predefined orientation against the object to be tested. The angle between the rod and the extension arm is, for example, set or fixed by hand before the extension arm is lifted, led to the object to be tested and applied with the guide against the object to be tested.

The described devices for positioning the collimator and a recording carrier, with a small number of elements, permit a flexible adaptation to a multitude of different conditions.

The first positioning means is basically also suitable, as a testing head holder, for positioning testing heads with other measurement principles. Such are for example ultrasound measurement heads or eddy current testing heads or temperature measurement heads or a camera (video or still picture) or an endoscope. With this, one may also carry out measurements without the second positioning means. In a corresponding further preferred embodiment of the invention, which is particularly suitable with these measurement principles, the first positioning means is thus designed for positioning a testing head with respect to an object to be tested. For this, the first positioning means comprises:

a rod for positioning the testing head;

a mechanical guide for centring the testing head with respect to an object to be tested;

an adjustable connection device, in particular a joint device, which connects the rod at a first end to the testing head and the mechanical guide, in an adjustable and fastenable manner;

wherein an alignment of the testing head at least between an angle perpendicular to the direction of the rod and an angle parallel to the rod and in the direction of the second end of the rod, may be set by way of the connection device.

With this, it is possible to lead the testing head in restricted conditions around an obstacle to a predefined location of the object to be tested. The device may be adapted to the obstacle present in each case, by way of setting the angle between the rod and the testing head.

Preferably, the joint device comprises two joints which may be rotated in each case about at least 90° and which may be locked, wherein the rotation axes of the 90° joints run parallel to one another. With this, a very high flexibility of the use with a simple and robust design is possible.

Preferably, the mechanical guide for centring the testing head is adjustable in a rotatable manner about a longitudinal axis of the guide which points to the object to be tested. With this, the device may be adapted to different orientations of the object to be tested.

In the method for use of the device designed as a testing head holder, the following steps are carried out:

setting and fixing a planned mutual position between the testing head and rod way of adjusting the connection device;

moving the device, preferably by hand, until the mechanical guide bears on the object to be tested in the desired position.

The movement of the device is effected preferably by way of one or more persons who hold a lower end of the rod, and by way of this move the connection device arranged at the upper end, with the testing head, into the desired measurement position.

Further preferred embodiments are to be deduced from the dependent patent claims. Thereby, features of the method claims may be combined with the device claims with regard to context, and vice versa.

BRIEF DESCRIPTION OF THE DRAWINGS

The invention is hereinafter explained in more detail by way of preferred embodiment examples, which are represented in the accompanying drawings. In each case schematically there are shown in.

The reference numerals used in the drawing and their significance are listed in a conclusive manner in the list of reference numerals. Basically, the same parts are provided with the same reference numerals in the figures.

WAYS OF CARRYING OUT THE INVENTION

Figure 1:
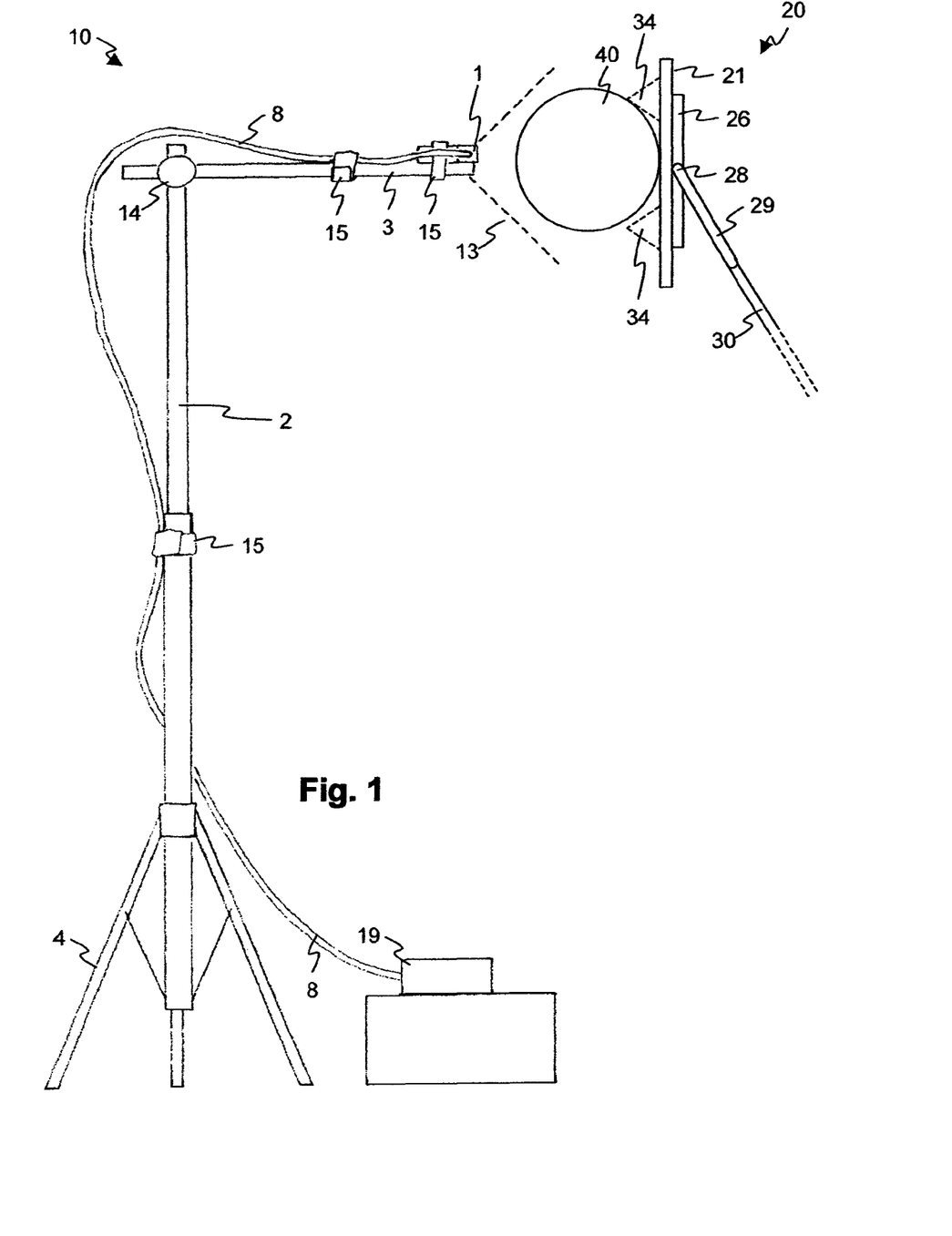
FIG. 1 a collimator holder and a part of a plate holder.
Figures 2, 3, 4:
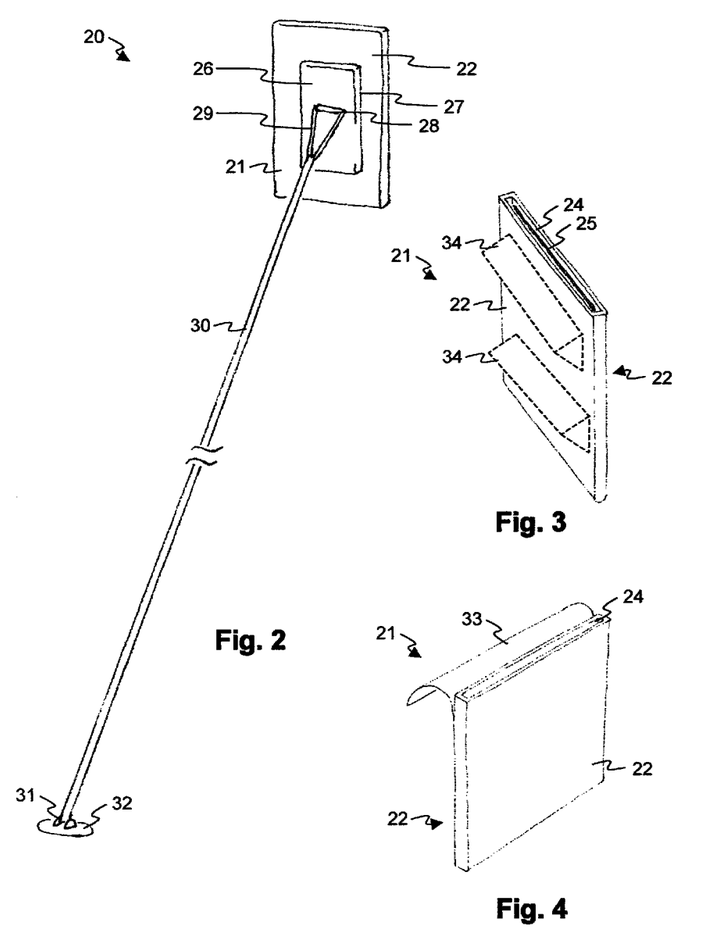
FIG. 2 a plate holder.
FIG. 3 a film holder.
FIG. 4 a variant of a film holder.

FIG. 1 shows a first embodiment of a collimator holder 10. The collimator holder 10 comprises a rod 2 with a length for example of two to six or nine or more meters. The rod 2 is preferably adjustable in length, and for this is preferably designed as a telescopic rod. The telescopic rod may be put together manually in a very simple manner, but also may be manually driven, electronically, pneumatically or hydraulically extendable. The rod 2 at the lower end is assembled in a stand 4, but may also be connected with a different type of anchoring. At the upper end, the rod 2 is connected to an extension arm 3 in a fixed manner or via an adjustable joint 14. The joint 3 has a length of up to 4 meters and carries a collimator 1. The collimator 1 is preferably fastened on the extension arm 3 with straps 15, in particular with Velcro fastener straps, or however for example with screw connections or clamping connections. The extension arm in another preferred embodiment of the invention, projects at the side lying opposite the collimator 1, beyond the rod 2 and is provided with a counter-weight to the collimator 1. In a further embodiment, a further rotation joint is arranged between the rod 2 and the collimator 1. In a preferred embodiment of the invention, the device comprises a mechanical guide 13 for centring the collimator 1 with respect to the axis of a pipe 40 to be examined. This is drawn in FIG. 1 in a dashed manner. The uppermost part of a plate holder 20 which is explained in more detail in the context of FIG. 2, is drawn on the side of the pipe 40 which lies opposite the collimator 1.

A radiation source in the known manner may be guided with a cable pull through a delivery tube 8 to the collimator 1. The delivery tube 8 may be shielded.

In order to convey the radiation source to the collimator 1, it is pushed in a manner known per se by way of a cable pull out of a shielded isotope container through a delivery tube 8 to the collimator 1. After the receipt, the radiation source is pulled back again to the isotope container by way of the cable pull. The pulling of the cable is preferably effected manually or with an electrical or other drive.

The collimator holder 10 thus acts as a first positioning means. At a first end, it comprises a collimator 1 and is movable by a person by way of firmly holding at the second end (which lies opposite the first end), wherein by way of this movement, the collimator 1 may be brought into a desired position with respect to an object 40 to be tested.

In an analogue fashion, the plate holder 20 acts as a second positioning means. It comprises, at a first end, an recording carrier or film holder 21 and is freely movable by way of a person firmly holding it at a second end (which lies opposite the first end), wherein by way of this movement, the recording carrier 21 may be brought into a desired position with respect to the object 40 to be tested.

FIG. 2 shows a plate holder 20, comprising a holding tube 30, at whose upper end a film holder 21 is fastened. At the lower end, the holding tube 30 may be fastened with a joint 31 to a foot plate 32 for an improved positioning. The holding tube is preferably a telescopic tube as is evident in FIG. 6. Preferably, the film holder 21 is releasably connected to a connection plate 26, and the connection plate 26 in turn is rotatably connected via a rotation joint 28, to a bow 29 of the holding tube 30. The rotation axis of the rotation joint 28 between the bow 29 and the connection plate 26 runs essentially perpendicularly to the longitudinal axis of the holding tube 30. With this, it is possible to hold the film holder 21 against a pipe 40 to be tested, wherein the inclination 21 of the film holder adapts 21 to the position of the pipe 40, independently of the inclination of the holding tube 30 to the position of the pipe 40.

The connection between the film holder 21 and the connection plate 26 is effected preferably by way of a Velcro connection, for example with a first Velcro connection material 22 (e.g. fluffy part) on the film holder 21, and second Velcro connection material 27 (e.g. hook part) on the connection plate 26. For this, preferably at least one side of the film holder, even better both sides, are covered over the complete surface with the Velcro connection material 22. Preferably, the outer side of the connection plate 26 is also coated over the whole surface with the corresponding Velcro connection material 27. The Velcro connection is thus stable, quick and simply releasable and comprises no metallic parts which could lead to sparks. Moreover, the film holder 21 is cushioned by the first Velcro connection material 22, and by way of this an occurring insulation of the pipe 40 is protected from damage. The material for the Velcro connections here, as also with the fastening straps 15, is preferably of anti-static material so that it may be applied in environments which are at risk from explosion. The complete-surface covering with Velcro material permits the connection plate to be positioned essentially at any location on the film holder.

FIG. 3 shows a film holder 21 as a recording carrier. The film holder 21 has a frame of a thin aluminium sheet-metal part, into which a film cassette 25 with an X-ray sensitive film may be inserted. In a preferred embodiment of the invention, the film holder 21 comprises guide bodies 34 (drawn dashed in FIGS. 1 and 3). The guide bodies 34 consist for example of hard foam, and are provided or covered with Velcro connection material. Thus the guide bodies 34 may be positioned at any position on a surface of the film holder 21, and may be adapted to the course of a pipe. On leaning the film holder 21 against the pipe, the position of the film holder 21 is thus additionally stabilised.

Other embodiments of guide bodies consist of aluminium sheet metal parts, for example in a size of approx. 5 cm times 20 cm. The aluminium sheet metal parts are preferably wrapped on all sides or at least in locations with Velcro-type material. By way of this, they may be bent into any desired shape and fixed at any location of the film holder 21.

FIG. 4 shows one variant of a film holder 21. This comprises a holding bow 33 with which the film holder 21 may be hung over a pipe 40. An improved stabilisation of the film holder 21 during the exposure results by way of this. The function of the bow may also be realised by way of the mentioned guide bodies of wrapped aluminium sheet metal parts.

Figure 5:
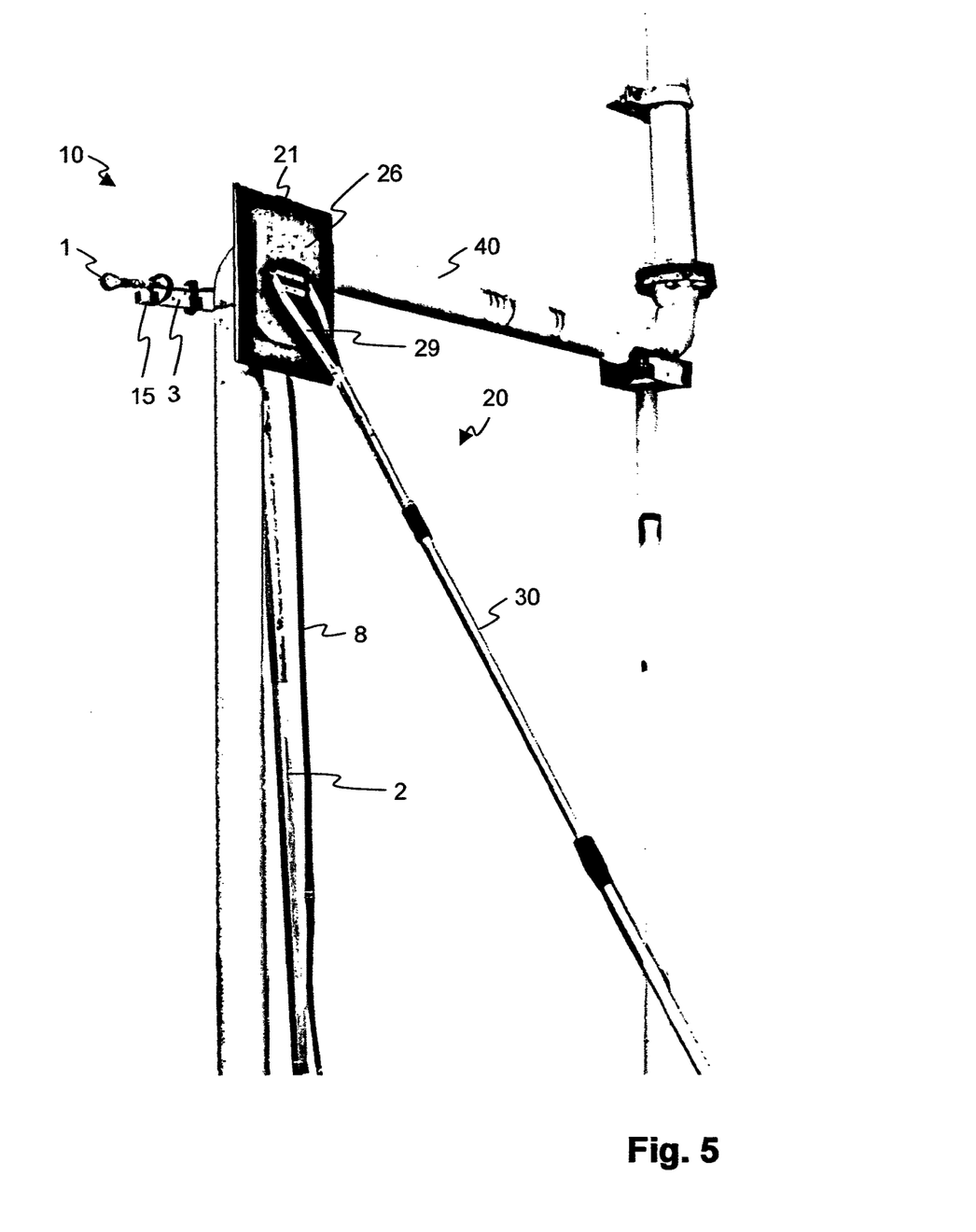
FIG. 5 the application of a device according to the invention.

FIG. 5 shows the application of the first embodiment of the device according to the invention. The collimator holder 10 is arranged with the collimator 1 at the end of the extension arm 3 on the one side of a pipe 40, the plate holder 20 with the film holder 21 on the opposite side. The plate holder 20 (not drawn) rests with the lower end on the base and rests against the pipe 40, thus as a whole is clamped between the base and the pipe 40 or is at least fixed by its intrinsic weight.

The film holder 21 is rotatable about a rotation axis with respect to the holding tube and, may be brought into a stable position—thus without tilting—with respect to the object to be tested by way of pressing the film holder 21 against the object to be tested and by way of the free rotation of the film holder 21 about the rotation axis of the joint 28 corresponding to the location at which the holding tube 30 or the connection plate 26 is fastened on the film holder For recording an X-ray picture of a pipe 40, one proceeds preferably as follows:

setting up the collimator holder 10 with the collimator 1 and delivery tube 8, setting up or leaning on the plate holder 20 with the film holder 21, if necessary, observing the safety distance by the operator, conveying the radiation source out of the isotope container 9 into the collimator 1 or activating the radiation source in the collimator 1 in another manner, conveying the radiation source back to the isotope container 9 or deactivating the radiation source.

Subsequently, the plate holder 20 is taken down and the X-ray picture is developed. The photograph may, for example, be repeated according to the result, or the collimator holder 10 displaced for the next photographing.

Figure 6:
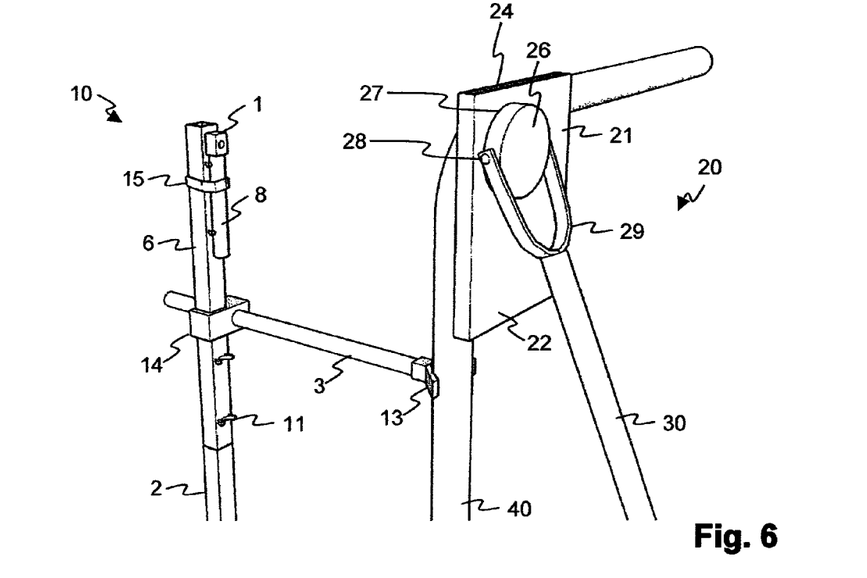
FIGS. 6 and 7 further examples for the application of the invention.
Figure 7:
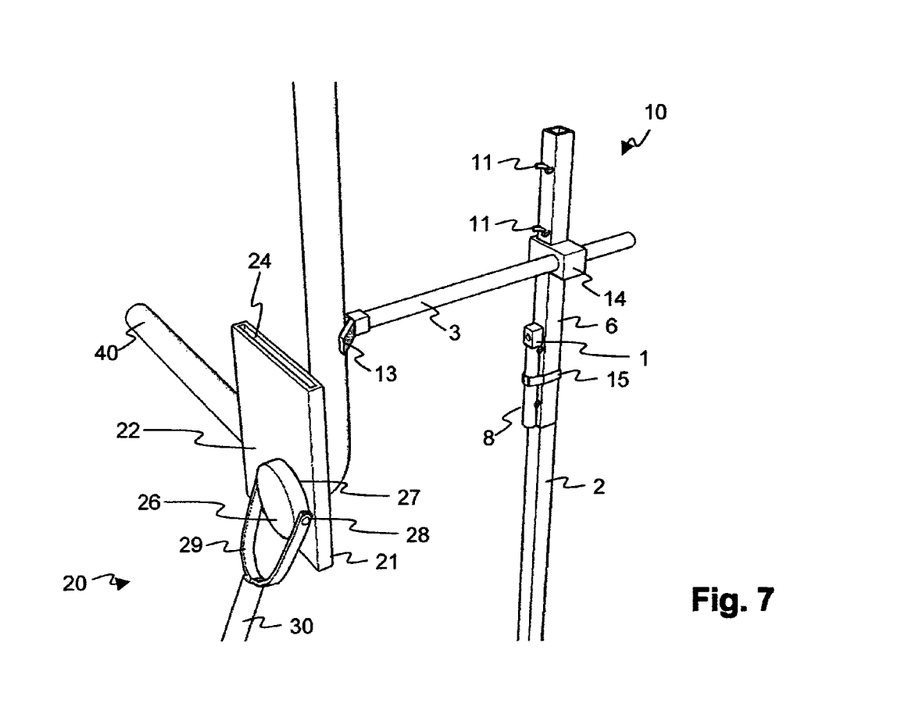
Figure 8:
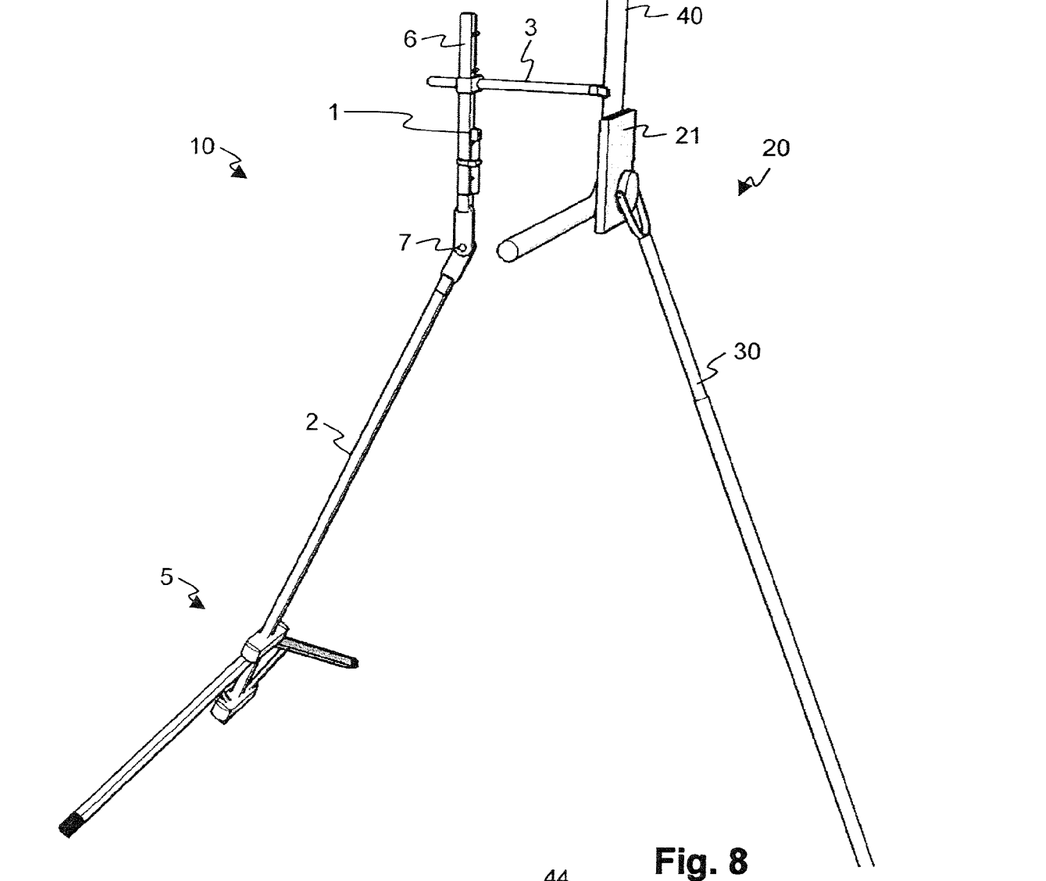
FIG. 8 the application of a third embodiment of the invention.

FIGS. 6 and 7 show further examples for the application of the invention. Therein, one may see how the guide 13 is preferably fastened on the rod 2 via an extension arm 3, and the collimator 1 in turn on the rod 2 or on an end piece 6 of the rod 2. The delivery tube 8 in the FIGS. 6 and 8 is only shown in part in the vicinity of the collimator 1. The guide 13 and the extension arm 3 set the distance between the collimator 1 and the object to be tested. The extension length of the extension arm 3, the position of the adjustable joint 14 and the position of the collimator 1 along the rod 2 or the end piece 6 is to be selected depending on the position of the section of the pipe 40 to be examined. The position of the connection plate 26 on the film holder 21 is also to be selected accordingly. The connection plate 26 here is round, in contrast to the rectangular connection plate of FIGS. 2 and 5. The connection to the film holder 21 here however is preferably also effected via a Velcro connection with the surface of the film holder 21 covered over the whole surface with Velcro connection material 22. In FIG. 6, the connection plate 26 is positioned in the left upper region of the film holder 21, so that the pressing point of the film holder 21 on the pipe arc leads to a stable position of the film holder 21. In contrast, in FIG. 7, the connection plate 26 is positioned in a right lower region of the film holder 21. With photographing at a T-connection of pipes, the connection plate 26 would tend to be arranged in the middle of the film holder 21.

The end piece preferably comprises fastening aids 11 for the secure fastening of the collimator 1 on the end piece 6. The fastening aids 11 are correspondingly shaped in the shape of the collimator 1, and form one or more mountings, in which the collimator 1 may be assembled in different positions and disassembled without and tools, for example with the help of Velcro fastener straps 15.

The adjustable joint 14 preferably also permits the guide 13 to rotate about the longitudinal axis of the extension arm 2. The orientation of the guide 13 may be adapted to e.g. a direction of the tube (horizontally, vertically or obliquely) by way of this.

FIG. 8 shows the application of a third embodiment of the invention. An end-piece 6 of the rod 2 is fastened to a first, upper end of the rod 2 in a rotatable manner by way of a rotation joint 7. The rotation axis of the joint 7 runs perpendicularly to the longitudinal axis of the rod 2. A bipod stand 5 is arranged at a second, lower end of the rod 2. By way of this, this collimator holder 10 may be tilted as a whole about the contact rest point of the bipod stand 5. In another embodiment of the invention, the rod 2 may likewise be tilted on a non-tiltable foot about an axis perpendicular to the longitudinal axis of the rod 2, by way of a rotation joint. The rod 2 with the collimator 1 may be led around a (non-shown) obstacle to the pipe 40 in restricted conditions by way of this, and with the guide 13 may be leaned onto the pipe 40. Basically, one may also arrange more than one rotation joint 7 between the rod 2 and the end piece 6, in order to achieve an increased flexibility.

Figure 9:
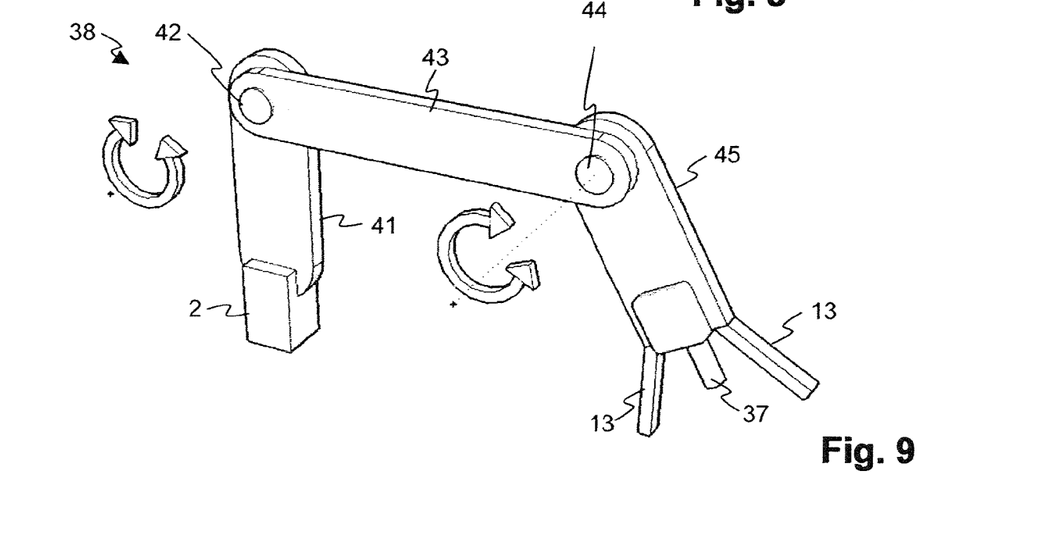
FIG. 9 a holder for a testing head.

FIG. 9 shows a holder for a testing head 37. The holder is a connection device 38 which may be fastened at the upper end of a rod 2 (for example of a stand). The connection device comprises a first member 41, on which a second member 43 is rotatably fasted via a rotation joint 44. In turn, a third member 45 is rotatably fastened on the second member 43 via a rotation joint. The testing head 3 is fastened on the third member 45 and preferably also a guide 13 for aligning the testing head 37 on a body to be examined. The two rotation joints 2, 4 are rotatable about axes which are parallel to one another by in each case 90° to 180° or even further, as indicated by two arrows, and the joints 4, 44 may be fixed, and also be realised by way of fixable ball joints.

An alignment of the testing head 37 at least between an angle perpendicular to the direction of the rod 2 and an angle parallel to the rod 2 and in the direction of the lower end of the rod 2 may be adjusted by way of the connection device 38.

The connection device 3 permits the testing head 37 to be guided from any side against e.g. a pipe 4 and to centre it.

LIST OF REFERENCE NUMERALS 1 collimator
2 rod
3 extension arm
4 stand
5 bipod stand
6 end-piece
7 rotation joint
8 delivery tube
9 isotope container
10 collimator container
11 fastening aid
13 guide
14 adjustable joint
15 Velcro fastener strap
18 opening in the shielding
19 cable pull device and isotope container
20 plate holder
21 film holder
22 Velcro connection material
24 slot
25 film cassette
26 connection plate
27 Velcro connection material
28 rotation joint
29 bow
30 holding tube
31 joint
32 foot plate
33 holding bow
34 guide body
35 joint foot
37 testing head
38 connection device
39 longitudinal axis of the guide
40 pipe
41, 43, 45 members
42, 44 joints

The invention claimed is:

1. A method for creating a radiographic recording, comprising the following steps:
Providing a device for radiographic, non-destructive testing of objects, including:
a first positioning means for positioning a collimator for receiving a radioactive radiation source, at an object to be tested, and
a second positioning means for positioning a recording carrier at the object to be tested, wherein the first positioning means can be at least one of anchored or set up, with a lower end on a rest surface, and the collimator is attached on an opposite, upper end;
wherein the first positioning means can be moved separately from the second positioning means and can be positioned independently of the second positioning means;
wherein the second positioning means comprises a holding tube for positioning the recording carrier with respect to the object to be tested;
wherein the recording carrier is rotatable about an axis perpendicular to a longitudinal axis of the holding tube of the second positioning means; and wherein the second positioning means is fastenable at different locations on a surface of the recording carrier by way of a releasable connection;

setting up the first positioning means with the collimator on one side of the object to be tested;

positioning a connection plate of the second positioning means on the recording carrier in a freely selectable position on a first surface of the recording carrier, and fixing the connection plate by way of a releasable connection;

setting up the second positioning means with the recording carrier on a side of the object to be tested, said side lying opposite the collimator, by positioning the second positioning means independently from the first positioning means; and thereby moving and leaning the recording carrier with a second surface of the recording carrier against the object to be tested, the recording carrier rotating freely about an axis with respect to a rod of the second positioning means, and the second surface of the recording carrier being opposite the first surface of the recording carrier;

bearing the recording carrier on the object to be tested in a stable position;

triggering a recording.

2. The method according to claim 1, wherein the step of setting up the first positioning means has the following steps:

setting and fixing a planned distance between the collimator and the object to be tested, by way of setting the mechanical guide, optionally also by way of the selection of the positioning of the collimator on the first positioning means;

moving the first positioning means, by hand, until the mechanical guide bears on the object to be tested, in the desired position.

3. The method according to claim 1, wherein the step of setting up the second positioning means comprises the following steps:

positioning guide bodies on a second surface of the recording carrier;

when moving and leaning the recording carrier against the object to be tested, the recording carrier being guided by the guide bodies bearing on the object to be tested.

4. The method according to claim 1, wherein the movement and leaning of the second positioning means is effected by way of one or more persons holding and moving a first end of the second positioning means, and by way of this move the recording carrier arranged at a second end of the second positioning means into the desired measurement position.

* * * * *